US012616205B2

(12) United States Patent
Deo

(10) Patent No.: US 12,616,205 B2
(45) Date of Patent: May 5, 2026

(54) SILVER-ION-IMPREGNATED CHANNEL FOR ENDOSCOPE, ENDOSCOPE INCLUDING SILVER-ION-IMPREGNATED CHANNEL, AND METHODS OF CLEANING AND REPROCESSING SUCH ENDOSCOPE

(71) Applicant: HOYA CORPORATION, Tokyo (JP)

(72) Inventor: Hrishikesh Deo, Brooklyn, NY (US)

(73) Assignee: HOYA CORPORATION, Tokyo (JP)

( * ) Notice: Subject to any disclaimer, the term of this patent is extended or adjusted under 35 U.S.C. 154(b) by 829 days.

(21) Appl. No.: 17/846,581

(22) Filed: Jun. 22, 2022

(65) Prior Publication Data

US 2023/0413827 A1    Dec. 28, 2023

(51) Int. Cl.
| | |
|---|---|
| *A01N 59/16* | (2006.01) |
| *A61L 2/208* | (2026.01) |
| *A61L 103/15* | (2026.01) |

(52) U.S. Cl.
CPC .............. *A01N 59/16* (2013.01); *A61L 2/208* (2013.01); *A61L 2103/15* (2026.01)

(58) Field of Classification Search
CPC ..... A01N 59/16; A61L 2/208; A61L 2202/24; A61B 1/015; A61B 1/018
See application file for complete search history.

(56) References Cited

U.S. PATENT DOCUMENTS

| | | | |
|---|---|---|---|
| 4,911,898 | A | 3/1990 | Hagiwara et al. |
| 5,505,887 | A | 4/1996 | Zdrahala et al. |

| | | | |
|---|---|---|---|
| 5,885,209 | A | 3/1999 | Green |
| 6,248,342 | B1 | 6/2001 | Trogolo et al. |
| 6,299,630 | B1 | 10/2001 | Yamamoto |
| 6,315,715 | B1 | 11/2001 | Taylor et al. |
| 6,464,632 | B1 | 10/2002 | Taylor |
| 6,689,122 | B2 | 2/2004 | Yamamoto |
| 6,866,859 | B2 | 3/2005 | Trogolo et al. |
| 6,939,820 | B2 | 9/2005 | Numaguchi et al. |
| 8,071,006 | B2 | 12/2011 | Thottupurathu |
| 8,080,490 | B2 | 12/2011 | Fechner et al. |
| 8,206,349 | B2 | 6/2012 | Slenker et al. |
| 8,609,036 | B2 | 12/2013 | Fuller et al. |
| 9,050,393 | B2 | 6/2015 | Saffran |
| 9,314,017 | B2 | 4/2016 | Myntti |
| 9,504,255 | B2 | 11/2016 | Cai |
| 9,561,294 | B2 | 2/2017 | Fuller et al. |

(Continued)

FOREIGN PATENT DOCUMENTS

| | | |
|---|---|---|
| EP | 1066839 A1 | 1/2001 |
| JP | 2004-262711 A | 9/2004 |

(Continued)

OTHER PUBLICATIONS

"Agion Active XL Advanced Odor Control Product Sheet", Sciessent LLC, 2015, 2 pages.

(Continued)

*Primary Examiner* — Aaron B Fairchild
(74) *Attorney, Agent, or Firm* — Greenblum & Bernstein, P.L.C.

(57) ABSTRACT

A channel for an endoscope comprises a tube made of polytetrafluoroethylene (PTFE) having at least one additive. The at least one additive includes a carrier that contains silver ions and is incorporated within a wall of the tube, and a content of silver ions in the tube is at least 0.0005% by weight of the tube.

8 Claims, 4 Drawing Sheets distal end 110    insertion tube 120    control portion 130
endoscope 100
interface portion 190    umbilical cord 180
electrical contacts 160
light guide 170    air/water port 140
suction nipple 150

(56) References Cited

U.S. PATENT DOCUMENTS

| | | | |
|---|---|---|---|
| 9,561,295 | B2 | 2/2017 | Fuller et al. |
| 9,566,359 | B2 | 2/2017 | Fuller et al. |
| 9,623,229 | B2 | 4/2017 | Coulson et al. |
| 9,821,094 | B2 | 11/2017 | Dehnad et al. |
| 10,265,435 | B2 | 4/2019 | Dehnad et al. |
| 10,420,822 | B2 | 9/2019 | Ivanova et al. |
| 10,682,431 | B2 | 6/2020 | Fuller et al. |
| 10,716,461 | B2 | 7/2020 | Jenkins |
| 10,758,596 | B2 | 9/2020 | Ivanova et al. |
| 11,020,508 | B2 | 6/2021 | Dehnad et al. |
| 2001/0025135 | A1* | 9/2001 | Naito ................. A61B 1/015 |
| | | | 600/156 |
| 2002/0068093 | A1 | 6/2002 | Trogolo et al. |
| 2004/0170700 | A1 | 9/2004 | Numaguchi et al. |
| 2005/0058682 | A1 | 3/2005 | Sharratt |
| 2005/0234297 | A1* | 10/2005 | Devierre ............ A61B 1/00087 |
| | | | 600/129 |
| 2006/0036130 | A1 | 2/2006 | Fitzpatrick |
| 2006/0259020 | A1 | 11/2006 | Sharratt |
| 2006/0264708 | A1 | 11/2006 | Horne |
| 2008/0086214 | A1 | 4/2008 | Hardin et al. |
| 2009/0252804 | A1 | 10/2009 | Koecher et al. |
| 2012/0083750 | A1 | 4/2012 | Sansoucy |
| 2014/0170238 | A1* | 6/2014 | Cliff ................... C09D 7/63 |
| | | | 424/618 |
| 2017/0274108 | A1 | 9/2017 | Vinteler |
| 2018/0116207 | A1 | 5/2018 | Mahadevan et al. |
| 2018/0206708 | A1* | 7/2018 | Miller ............... A61B 1/00177 |
| 2018/0249903 | A1 | 9/2018 | Strombergsson et al. |
| 2020/0030477 | A1 | 1/2020 | Boyden et al. |
| 2020/0123370 | A1 | 4/2020 | Qu et al. |
| 2021/0153728 | A1 | 5/2021 | Polluks et al. |

FOREIGN PATENT DOCUMENTS

| | | | |
|---|---|---|---|
| JP | 2006218209 | A | 8/2006 |
| JP | 2006223475 | A | 8/2006 |
| JP | 2010043241 | A | 2/2010 |
| KR | 20090107428 | A | 10/2009 |
| KR | 101103758 | B1 | 1/2012 |
| WO | 0137670 | A2 | 5/2001 |
| WO | 2018150252 | A1 | 8/2018 |

OTHER PUBLICATIONS

"Agion Antimicrobial Field to Factory Direct Communication", MKT Metal Manufacturing, 2020, 9 pages.

"Combat Product Data Sheet", retrieved from the internet https://www.fosterpolymers.com/additives/Combat%20Product%20Data%20Sheet.pdf, retrieved on Jul. 7, 2022, 2 pages.

"Combat Product Data Sheet Rev 1-0719", Retrieved from the internet https://www.fostercomp.com/wp-content/uploads/2020/01/Combat-Product-Data-Sheet_Rev1-0719-_Digital.pdf, retrieved on Jul. 7, 2022, 2 pages.

"Fluon—The extrusion of PTFE granular powders", Technical Service Note F2, AGC Chemicals Americas Inc., 2002, 37 pages.

"Fluoropolymergroup—Introduction into the processing of PTFE resins", Retrieved from the internet https://www.pro-kunststoff.de/assets/Merkbl%C3%A4tter%20und%20Co/TM%2002%20Introduction%20into%20the%20processing%20of%20PTFE%20resins%20(February%202020).pdf retrieved on Jul. 7, 2022, Feb. 2020, 30 pages.

"Phosphate Glass—Wikipedia", Retrieved from the internet https://en.wikipedia.org/wiki/Phosphate_glass retrieved on Jul. 7, 2022, 2 pages.

"Sciessent—Agion Antimicrobial Efficacy Against Coronavirus is Tested and Published", Retrieved from the internet https://www.sciessent.com/wp-content/uploads/2020/03/Sciessent-Coronavirus-Whitepaper.pdf retrieved on Jul. 7, 2022, 3 pages.

"Sciessent—Agion Sell Sheet", Retrieved from the internet https://www.sciessent.com/wp-content/uploads/2021/10/Sciessent-Agion-SellSheet.pdf retrieved on Jul. 7, 2022, 3 pages.

Ahmed, "Developing unique geometries of phosphate-based glasses and their prospective biomedical applications", Johnson Matthey Technology Review 63.1, 2018, 34-42.

Armentano et al., "The interaction of bacteria with engineered nanostructured polymeric materials: a review", The Scientific World Journal 2014, 2014, 19 pages.

Brandt-Wunderlich et al., "A method to determine the kink resistance of stents and stent delivery systems according to international standards", Current Directions in Biomedical Engineering 2.1, 2016, 289-292.

Chen et al., "Superior ion release properties and antibacterial efficacy of nanostructured zeolites ion-exchanged with zinc, copper, and iron", RSC advances 8.66, 2018, 37949-37957.

Cowen et al., "Antimicrobial Efficacy of a Silver-Zeolite Matrix Coating on Stainless Steel", Carrier Corporation, Syracuse, New York, Apr. 2003, 11 pages.

Dutta et al., "Zeolite-supported silver as antimicrobial agents", Coordination Chemistry Reviews 383, 2019, 29 pages.

Estores et al., "Silver hydrogel urinary catheters: evaluation of safety and efficacy in single patient with chronic spinal cord injury", Journal of Rehabilitation Research & Development 45.1, 2008, 135-140.

Guo et al., "Effect of surface modification on the adhesion enhancement of electrolessly deposited Ag-PTFE antibacterial composite coatings to polymer substrates", Materials Letters 143, 2015, 256-260.

Karchmer et al., "A randomized crossover study of silver-coated urinary catheters in hospitalized patients", Archives of Internal Medicine 160.21, 2000, 3294-3298.

Kyffin et al., "Antibacterial silver-doped phosphate-based glasses prepared by coacervation", Journal of Materials Chemistry B 7.48, 2019, 7744-7755.

Lai et al., "Efficacy of antimicrobial-impregnated catheters for prevention of bloodstream infections in pediatric patients: a meta-analysis", Frontiers in Pediatrics 9, Article 632308, May 31, 2021, 7 pages.

Lai et al., "Catheter impregnation, coating or bonding for reducing central venous catheter-related infections in adults (Review)", Cochrane Database of Systematic Reviews 2016, Issue 3. Art. No. CD007878, 2016, 148 pages.

Lee et al., "Fabrication of a silver particle-integrated silicone polymer-covered metal stent against sludge and biofilm formation and stent-induced tissue inflammation", Scientific reports 6.1, 2016, 11 pages.

Moloney, "A Guide to Leveraging Antimicrobials to Protect the Surfaces of Medical Devices", Sciessent LLC, 2015, 5 pages.

Muñoz et al., "Phosphate glasses", Springer Handbook of Glass; Springer, Cham, 2019, 553-594.

Pittol, "Antimicrobial performance of thermoplastic elastomers containing zinc pyrithione and silver nanoparticles", Materials Research 20, 2017, 1266-1273.

Raja et al., "Synergistic Antimicrobial Metal Oxide-Doped Phosphate Glasses; a Potential Strategy to Reduce Antimicrobial Resistance and Host Cell Toxicity", ACS Biomaterials Science & Engineering 8.3, 2022, 1193-1199.

Raja et al., "The antimicrobial efficacy of zinc doped phosphate-based glass for treating catheter associated urinary tract infections", Materials Science and Engineering: C 103, 109868, 2019, 9 pages.

Rivadeneira et al., "Bioactive glasses as delivery systems for antimicrobial agents", Journal of applied microbiology 122.6, 2017, 1424-1437.

Schmitz et al., "In vitro studies of encrustations on catheters, a model of infection stone formation", Cells and Materials 3.1, 1993, 10 pages.

Sieh et al., "Non-cyanide electrodeposited Ag-PTFE composite coating using direct or pulsed current deposition", Coatings 6.3, 2016, 14 pages.

Škrlová, "Biocompatible polymer materials with antimicrobial properties for preparation of stents", Nanomaterials 9.11, 1548, 2019, 31 pages.

Turner et al., "Use of silver-based additives for the development of antibacterial functionality in Laser Sintered polyamide 12 parts", Scientific reports 10.1, 2020, 11 pages.

(56) References Cited

OTHER PUBLICATIONS

Valappil et al., "Effect of silver content on the structure and antibacterial activity of silver-doped phosphate-based glasses", Antimicrobial agents and chemotherapy 51.12, 2007, 4453-4461.

Valappil et al., "Effect of silver-doped phosphate-based glasses on bacterial biofilm growth", Applied and environmental microbiology 74.16, 2008, 5228-5230.

Wang et al., "Effectiveness of antimicrobial-coated central venous catheters for preventing catheter-related blood-stream infections with the implementation of bundles: a systematic review and network meta-analysis", Annals of intensive care 8.71, 2018, 12 pages.

Wang et al., "In-vitro antibacterial and anti-encrustation performance of silver-polytetrafluoroethylene nanocomposite coated urinary catheters", Journal of Hospital Infection 103.1, 2019, 55-63.

Wassil et al., "Antimicrobial impregnated catheters in the prevention of catheter-related bloodstream infection in hospitalized patients", The Journal of Pediatric Pharmacology and Therapeutics 12.2, 2007, 77-90.

Zhang et al., "Enhanced antibacterial and antiadhesive activities of silver-PTFE nanocomposite coating for urinary catheters", ACS Biomaterials Science & Engineering 5.6, 2019, 2804-2814.

PCT/US2023/026007, "International Search Report and Written Opinion", Oct. 16, 2023, 9 pages.

Office Action, mailed Nov. 11, 2025, in corresponding Japanese Application No. 2024-572269.

* cited by examiner

SILVER-ION-IMPREGNATED CHANNEL FOR ENDOSCOPE, ENDOSCOPE INCLUDING SILVER-ION-IMPREGNATED CHANNEL, AND METHODS OF CLEANING AND REPROCESSING SUCH ENDOSCOPE

BACKGROUND

Field

The present disclosure generally relates to surgical devices, methods of fabrication of surgical devices, and methods of use of surgical devices. More particularly, and without limitation, the disclosed embodiments relate to endoscope channels (e.g., working channels) impregnated with silver ions, devices and systems having such a channel, and methods for manufacture, assembly, or use of such devices, systems, or channels.

Background

An endoscope is a surgical instrument that may be used to access (e.g., view or remove) or treat tissue within the body of a patient by inserting one or more medical tools into the body through an incision in the body or an orifice of the body.

SUMMARY

A channel for an endoscope according to a general configuration comprises a tube made of polytetrafluoroethylene (PTFE) having at least one additive. The channel may be at least one among an air channel for an endoscope, a water channel for an endoscope, or a working channel for an endoscope. The at least one additive includes a carrier that contains silver ions and is incorporated within a wall of the tube, and a content of silver ions in the tube is at least 0.0005% by weight of the tube. Endoscopes comprising at least one such channel, and methods of reprocessing (e.g., cleaning and/or disinfecting) such endoscopes, are also disclosed.

DETAILED DESCRIPTION

The disclosed embodiments include silver-ion-impregnated channels for endoscopes, and endoscopes including silver-ion-impregnated channels. Advantageously, embodiments of the present disclosure allow for a durable antimicrobial effect to inhibit biofilm formation and serve as an adjunct solution to a cleaning and disinfection routine.

As described herein, an endoscope typically includes a control portion (e.g., a handle) at a proximal end, a distal (or "sensing") end, and an insertion tube that extends between the control portion and the distal end. The insertion tube houses a tube called a "working channel" that defines an interior lumen. In some cases, the working channel may define more than one interior lumen (e.g., in parallel). The term "proximal" (e.g., "a proximal end") refers to a point or a location along the length of the endoscope that is to closer to a physician or other medical practitioner during use of the endoscope, and the term "distal" (e.g., "a distal end") refers to a point or location along the length of the endoscope that is to be closer to a location of tissue being viewed or treated within the body of a patient during use of the endoscope. Types of endoscope include, for example and without limitation, bronchoscopes, sinuscopes, nasopharyngoscopes, laryngoscopes, laparoscopes, gastroscopes, duodenoscopes, colonoscopes, hysteroscopes, cystoscopes, uroscopes, urethroscopes, cardioscopes, and arthroscopes.

Figure 1:
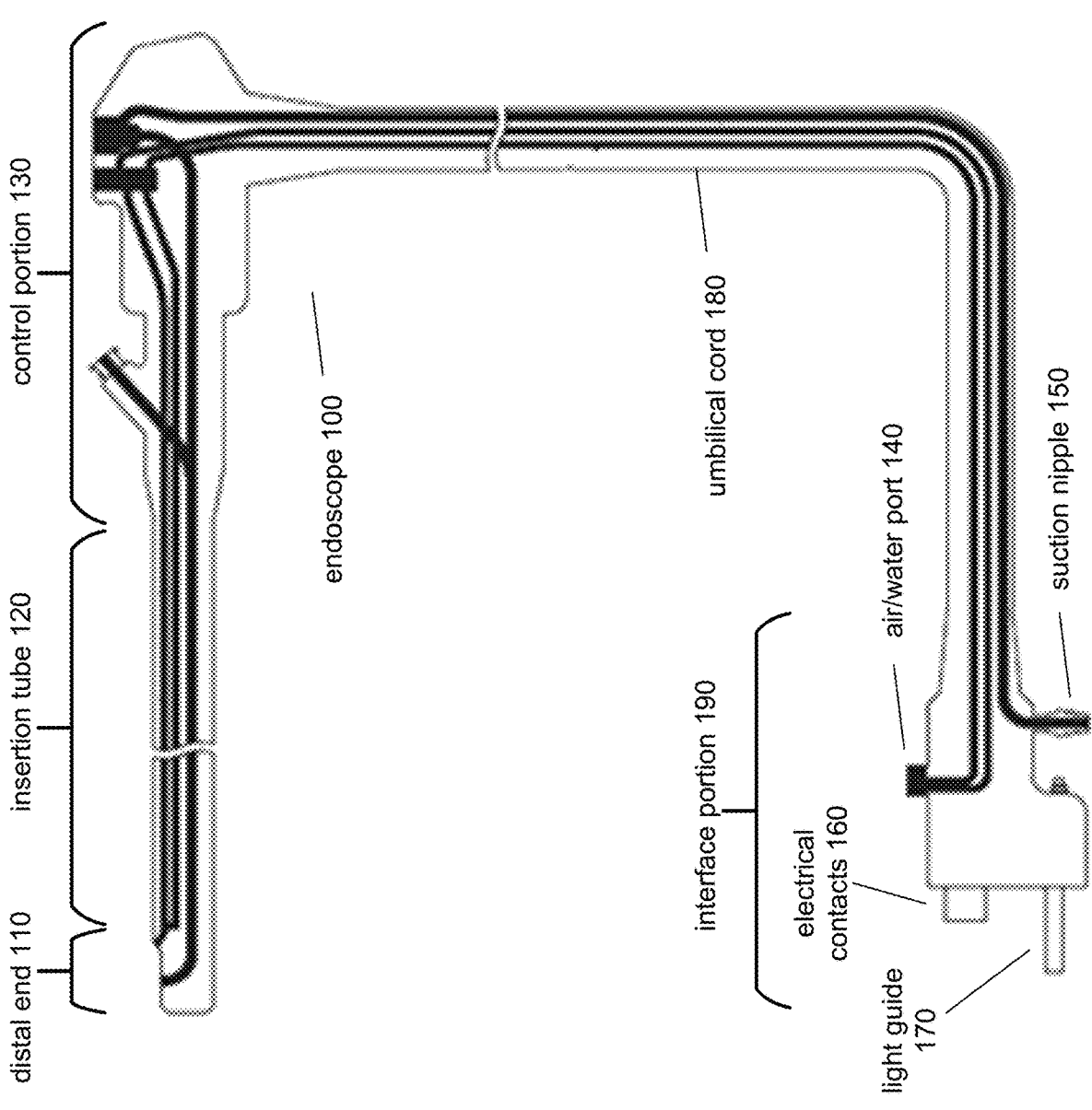
FIG. 1 is a diagram showing parts of an endoscope.

FIG. 1 is a diagram showing parts of an endoscope 100. Endoscope 100 includes a control portion 130 that is connected to a distal end 110 by a insertion tube 120. Control portion 130 is also connected to an interface portion 190 via an umbilical cord 180. In this example, the interface portion 190 includes an air/water port 140, a suction nipple 150, electrical contact 160, and/or a light guide 170. FIG. 1 also shows an example of a configuration of interior channels of the endoscope 100.

The working channel of an endoscope may also be called an instrument channel, a tool channel, or a biopsy channel. During use of the endoscope, a medical instrument or tool (e.g., a forceps, needle, scissors, grasper, retractor, snare, dilator, or brush) may be introduced into the working channel of the endoscope from the proximal end (e.g., via a working channel inlet) to the distal end of the endoscope until a distal end of the tool approximates or reaches a desired location for accessing or treating tissue of the patient (e.g., to perform a surgical operation inside the body, to retrieve a tissue sample via the working channel, etc.).

The diameter of the working channel typically depends on the outer diameter of the endoscope (e.g., the outer diameter of the insertion tube 120). Depending on, for example, the type of endoscope, the working channel may have an inner diameter (e.g. an inner diameter of a tube of the working channel) in the range of from about one mm to about eight mm, in one example from about one mm to about five mm. The inner diameter of the channel may for example be at least three millimeters, in some examples at least four millimeters, in one example at least five millimeters. In other examples, the inner diameter of the channel may be not more than three millimeters, in some examples not more than two millimeters, in one example not more than 1.5 mm. More specifically, the working channel may have an inner diameter of about 1.2 mm, of about 2.8 mm (e.g. for a gastroscope), of about 3.2 mm (e.g., for a colonoscope (34Fr)), of about 3.8 mm (e.g., for a colonoscope (38Fr)), or of about 4.2 mm (e.g., for a duodenoscope). The inner diameter of the working channel is typically substantially constant along the length of the channel. In an endoscope for gastroenterological use (e.g., a gastroscope, a duodenoscope, a colonoscope), the working channel may have a length of up to approximately one or one-and-a-half meters (as measured from the working channel inlet at the control portion to the working channel outlet at the distal end). The ratio of inner diameter to outer diameter of the working channel may be in the range of from 0.75 to 0.85.

When the insertion tube is in a straight configuration (as shown in FIG. 1, for example), the working channel extends within the insertion tube such that the longitudinal axis of the working channel is parallel or substantially parallel to the longitudinal axis of the insertion tube. When the insertion tube is bent (e.g., during use of the endoscope), the working channel bends accordingly, such that the shape of the working channel may depend on how the endoscope is flexed. The endoscope may include one or more articulation mechanisms that may be used to bend the insertion tube during use of the endoscope.

The working channel may also be configured to function as a suction channel (e.g., to suction fluid from within the body), or the endoscope may include a suction channel that is separate from the working channel. An endoscope may have more than one working channel.

An endoscope may include one or more additional channels to provide further capabilities. For example, an endoscope may include one or more air channels, which may be used to provide insufflation of air or carbon dioxide at the distal end (e.g. for better visibility). Additionally or alternatively, an endoscope may include one or more water channels, which may be used to provide water to the distal end (e.g., for irrigation of a wound site, for lens cleaning). An endoscope may include a combined air/water channel. The inner diameter of an air channel, a water channel, or an air/water channel of the endoscope may be comparable or similar to (e.g., within 5 or 10 percent of) the inner diameter of the working channel of the endoscope, in particular for a small endoscope. In other examples, the inner diameter of an air channel, a water channel, or an air/water channel of an endoscope may be more narrow than (e.g., may be between ten and fifty percent of, in some examples as little as thirty percent of) the inner diameter of the working channel of the endoscope, in particular for a large endoscope (e.g., as for gastroenterological use). The inner diameter of each such channel is typically substantially constant along the length of the channel. The ratio of inner diameter to outer diameter of each such channel may be in the range of from 0.7 to 0.8. The length of an air channel, a water channel, or an air/water channel in an endoscope may be comparable or similar to (e.g., within 5 or 10 percent of) the length of the working channel of the endoscope.

Figure 2:
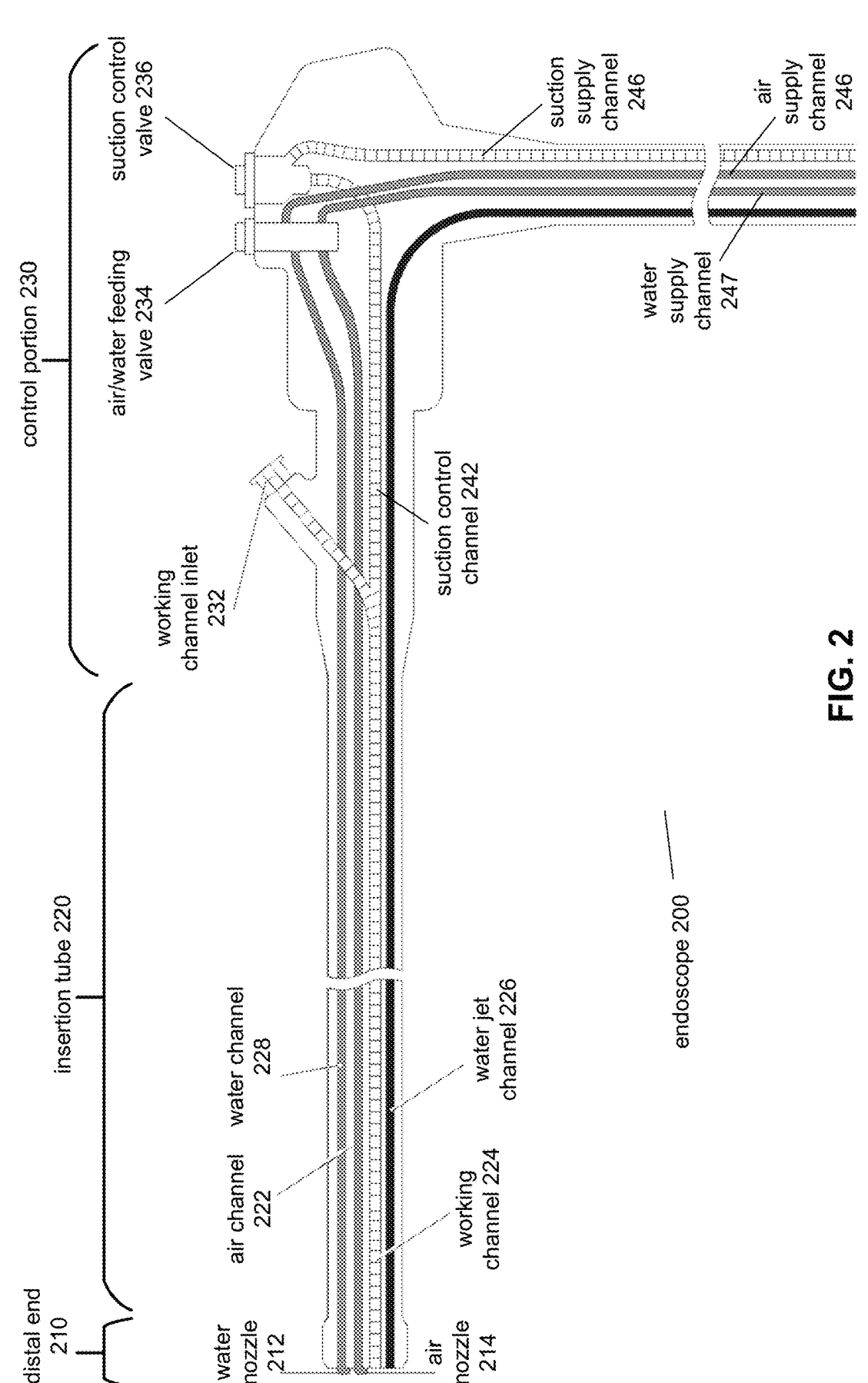
FIG. 2 is a diagram that shows an example of interior channels of an endoscope.

FIG. 2 is a diagram that shows an example of interior channels of an endoscope 200. Endoscope 200 includes a control portion 230 that is connected to a distal end 210 by an insertion tube 220. The insertion tube 220 houses a working channel 224, which extends between a working channel inlet 232 at the control portion 230 and a working channel outlet (not labeled) at the distal end 210. The insertion tube 220 may also house an air channel 222, which extends between an air/water feeding valve 234 at the control portion 230 and an air nozzle 214 at the distal end 210, and/or a water channel 228, which extends between the air/water feeding valve 234 at the control portion 230 and a water nozzle 212 at the distal end 210. In this example, the endoscope 200 may additionally or alternatively also include a water jet channel 226 that extends between a water jet port (not labeled) at an interface portion (not shown) of the endoscope 200 and a corresponding outlet (not labeled) at the distal end 210.

Figure 3:
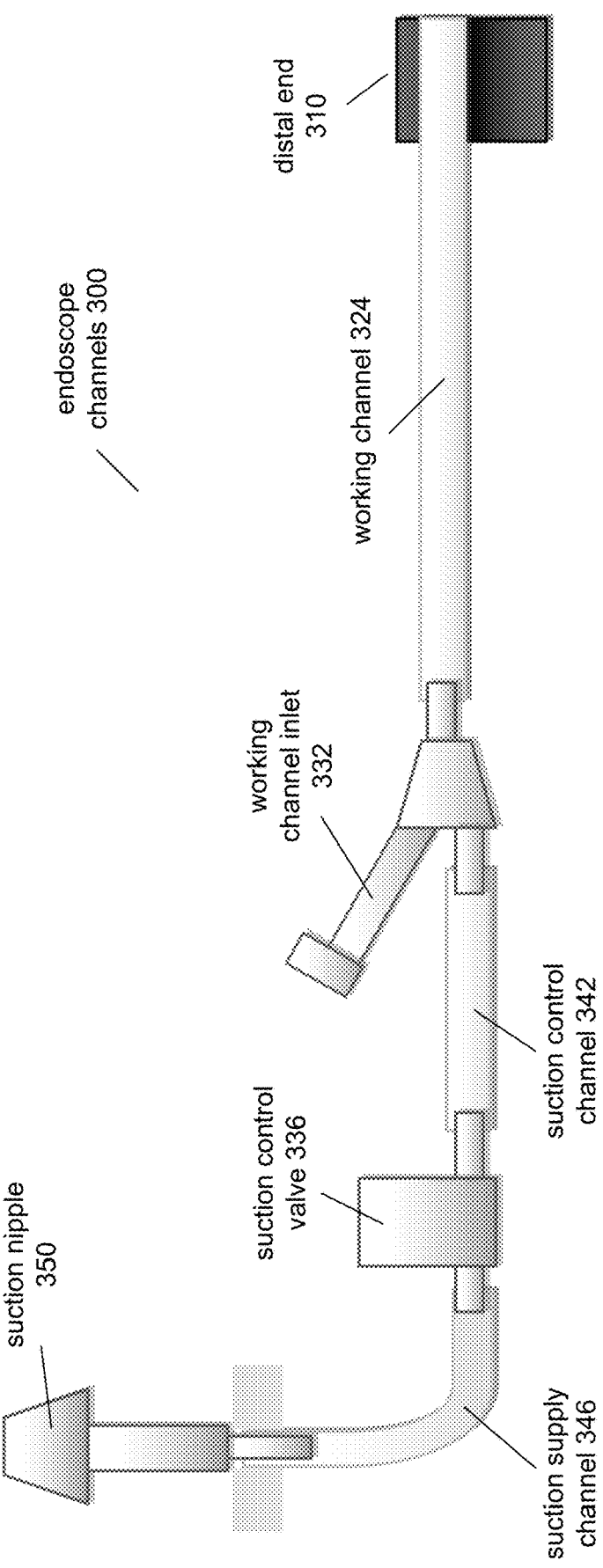
FIG. 3 is a diagram that shows another example of channels of an endoscope.

FIG. 3 is a diagram that shows another example 300 of channels of an endoscope. This example shows components of a working channel and suction system that includes a working channel 324, which extends between a working channel inlet 332 (e.g., at a control portion of the endoscope) and a working channel outlet (not labeled) at the distal end 310; a suction control channel 342, which extends between the working channel inlet 332 and a suction control valve 336 (e.g., at the control portion of the endoscope); and a suction supply channel 346, which extends between the suction control valve 336 and a suction nipple 350 (e.g., at an interface portion of the endoscope). FIG. 3 is a schematic representation, and the relative dimensions of the components as illustrated in this figure are not depicted to scale. For a large endoscope (e.g., as for gastroenterological use), the length of the suction supply channel may be comparable or similar to (e.g., within 5 or 10 percent of) the length of the working channel; the length of the suction control channel may be in a range of from eighty to 125 millimeters; the inner diameter of the suction supply channel and/or of the suction control channel may be in the range of from three to five (e.g., 3.2, 4.0, in some examples in the range of from 3.2 to 4.0) millimeters; and/or the ratio of inner diameter to outer diameter of the suction supply channel and/or of the suction control channel may be in the range of from 0.75 to 0.85.

Figure 4:
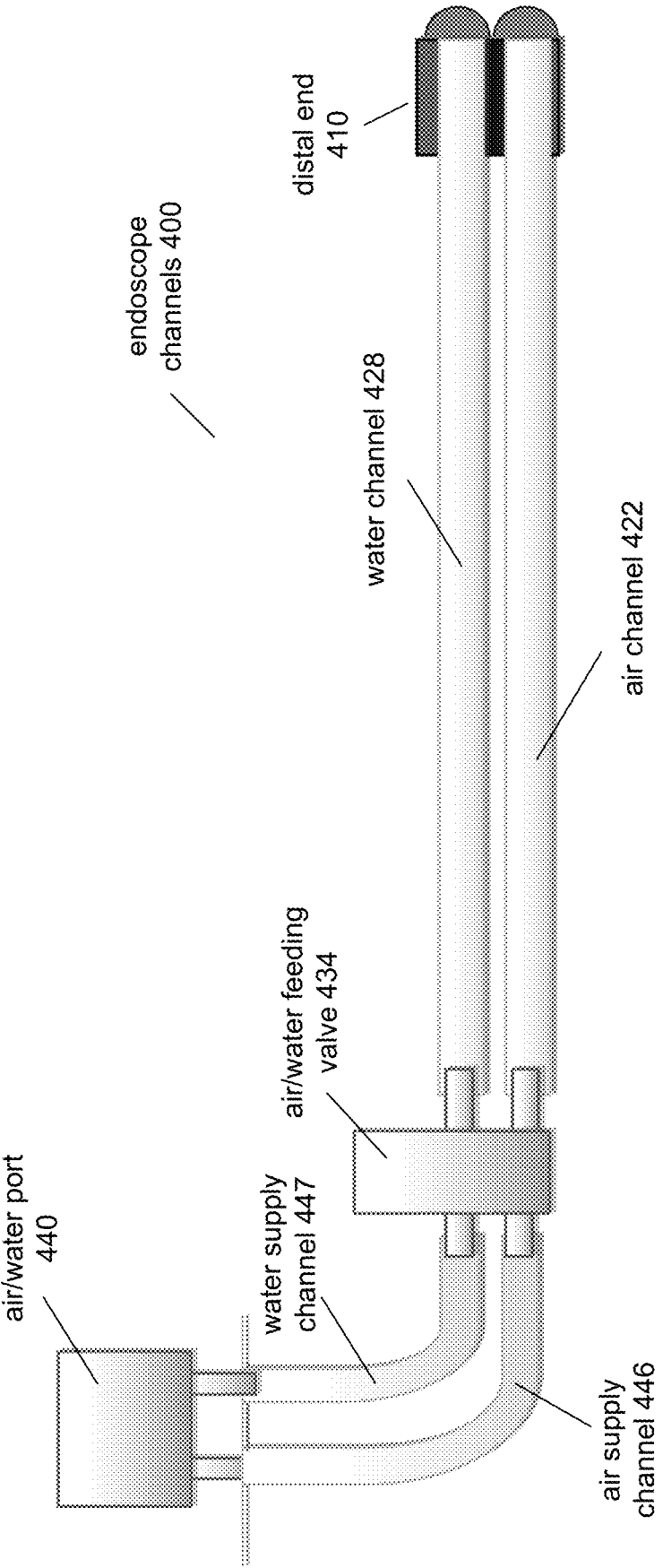
FIG. 4 is a diagram that shows a further example of channels of an endoscope.

FIG. 4 is a diagram that shows another example 400 of channels of an endoscope. This example shows components of an air and water channel system that includes an air channel 422, which extends between an air/water feeding valve 434 (e.g., at a control portion of the endoscope) and an air nozzle (not labeled) at the distal end 410; a water channel 428, which extends between the air/water feeding valve 434 and a water nozzle (not labeled) at the distal end 410; an air supply channel 446, which extends between the air/water feeding valve 434 and an air/water port 440 (e.g., at an interface portion of the endoscope); and a water supply channel 447, which also extends between the air/water feeding valve 434 and the air/water port 440. FIG. 4 is a schematic representation, and the relative dimensions of the components as illustrated in this figure are not depicted to scale. The length of the air channel and/or of the water channel of an endoscope may be comparable or similar to (e.g., within 5 or 10 percent of) the length of the working channel of the endoscope. For a large endoscope (e.g., as for gastroenterological use), the length of the air supply channel and/or of the water supply channel also may be comparable or similar to (e.g., within 5 or 10 percent of) the length of the working channel.

The working channel of an endoscope may be implemented as a tube made of (e.g. comprising or consisting of) polytetrafluoroethylene (PTFE), which is smooth, durable, and exceptionally nonreactive. Additionally or alternatively, the interior lumen of the working channel of an endoscope may be lined with a tube made of PTFE. Similarly, an air, water, or air/water channel of an endoscope may be implemented as a tube made of PTFE, and/or its interior lumen may be lined with a tube made of PTFE. Similarly, a suction control channel, a suction supply channel, an air supply channel, and/or a water supply channel of an endoscope may be implemented as a tube made of PTFE, and/or the interior lumen of such a channel may be lined with a tube made of PTFE. In some examples, the tube may be made of a different thermoplastic polymer, in particular a different fluoropolymer, other than PTFE, e.g. instead of or in addition to PTFE.

Because an endoscope is used within the body, it is expected that it will become contaminated by such use and must undergo reprocessing (e.g., cleaning, disinfection, and/or sterilization) before the next use. Contamination may be expected to occur especially in the working channel: for example, as used instruments or tissue samples are withdrawn from the body via the channel, or as fluids are suctioned out from the body via the channel. Cleaning of the endoscope may include brushing of the working channel and/or forcing a detergent or other surfactant and/or disinfecting solution through each of one, some, or all of the air, water, air/water, and/or working channels. Typically an air, water, or air/water channel is too narrow to accommodate a cleaning brush.

Use and cleaning of the endoscope may cause cumulative microdamage to the working channel. As instruments or tools (typically made of metal) pass through the working channel, they may scratch or abrade the inner surface of the channel. Brushing of the channel during cleaning may also increase the surface roughness of the inner surface of the channel. Although such microdamage may not affect the utility of the endoscope, it may lead to an increased tendency of biofilm formation over time. A biofilm is formed when bacteria adhere to a surface and develop a polymer matrix that enables additional bacteria and other microorganisms to accumulate into a persistent community. The bacteria within a biofilm are much more resistant to antimicrobial substances than planktonic (free-living) bacteria.

A risk of biofilm formation may be present in other channels as well, for example in an air, water, or air/water channel. Such a channel may be too narrow to brush, so that cleaning of the channel is typically performed by forcing a cleaning solution (e.g., a solution containing at least one detergent and/or enzymatic cleaning agent) at pressure through the channel. Such a cleaning technique may be less effective at dislodging biofilm or other adhesions than brushing.

Cleaning of an endoscope channel (e.g., any one or more of the endoscope channels described herein) may include injecting, into the interior lumen of the channel, a flow of a dispersion (e.g., a suspension), in a gas, of fine droplets of a liquid. The gas may comprise or consist essentially of, for example, one or more of air, dinitrogen, or carbon dioxide. The liquid may comprise or consist essentially of, for example, one or more of osmosed water, distilled water, deionized water, or purified water (e.g., type II laboratory grade purified water). In one example, a concentration of surfactants in the liquid does not exceed 2 mg/L. The flow may be turbulent (e.g., may have a Reynolds number higher than 2300, such as in a range of from 3500 to 100,000). The flow may be obtained from an output of a atomization chamber. A gas flow rate of the flow may be in the range of from ten to one hundred liters per minute. A concentration of the liquid droplets in the flow may vary over time (e.g., at a frequency in the range of from three to three hundred cycles per minute). Such variation may for example be produced by providing the liquid to the atomization chamber as pulsed discharges while providing the gas to the atomization chamber as a continuous flow. The injecting may be performed continuously over a duration in the range of, for example, from sixty to six hundred seconds.

After the endoscope has been cleaned, it may undergo a high-level disinfection (HLD) routine as well. The HLD routine may include soaking the endoscope in a disinfecting solution that contains at least one high-level disinfectant. The high-level disinfectant may for example be configured to eliminate microorganisms (e.g. bacteria) in or on the endoscope or a part thereof. Examples of high-level disinfectants that may be contained in the disinfecting solution include glutaraldehyde (e.g., at a concentration of 2% or more, 2.4% or more, 3% or more), ortho-phthalaldehyde (OPA; e.g., at a concentration of 0.5% or higher, 0.55% or higher, 0.6% or higher), and peracetic acid (e.g., at a concentration of between 0.1% and 0.3%, e.g. about 0.2%). After cleaning and/or after HLD, one or more channels of the endoscope (e.g., any one or more of the endoscope channels described herein) may be dried by injecting a gas at a low flow rate (e.g., in a range of from one to twenty liters per minute) at a low to moderate temperature (e.g., in a range of from ten to thirty degrees Celsius) to remove residual water (e.g., for a duration of from ten to sixty seconds), and then at a high flow rate (e.g., in a range of from twenty to one hundred liters per minute) at a moderate to high temperature (e.g., in a range of from thirty to sixty degrees Celsius) (e.g., for a duration of from thirty to 150 seconds). The gas may comprise or consist essentially of, for example, at least one of dinitrogen or air. During the high-flow-rate period, the gas may be a plasma (e.g., generated by an electrical discharge in a flow of dinitrogen or air), which may disinfect the channel. In such case, the temperature of the plasma may be in a range of from twenty to eights degrees Celsius (e.g., in a range of from thirty to fifty degrees Celsius), and a duration of the plasma-injecting period may be in a range of from five to sixty seconds.

Additionally or alternatively to HLD, the endoscope may be confined within a sterilizing environment (e.g., vaporized hydrogen peroxide) for a specified period to neutralize any biofilm or other contamination that may remain after cleaning. Such a regimen of cleaning and HLD and/or sterilization after each use has been shown to reduce the risk of cross-contamination to well below the maximum levels permitted by regulation. Nevertheless, it may be desired to further inhibit biofilm formation in a manner that remains effective after many use cycles.

Antimicrobial coatings have been applied to medical devices that are intended for use within the human body, such as catheters. Although it may be possible to apply an antimicrobial coating to the interior surface of a working channel, e.g. a PTFE working channel, of an endoscope (and/or one or more other channels of the endoscope), such a coating may not be sufficiently durable to withstand repeated use and cleaning cycles, and its use may lead to flaking or other failures of adhesion. The efficacy of such a coating may also decrease too rapidly over time to be practical.

Embodiments disclosed herein include a channel, in particular a working channel, for an endoscope, or a liner for a channel, in particular a working channel, for an endoscope, that is made of a tube of PTFE (or another thermoplastic polymer) and incorporates an antimicrobial additive (e.g., as opposed to a tube of PTFE that has an antimicrobial coating). The antimicrobial additive may for example be embedded in the substance or material of the channel (or tube), e.g. in a wall of the channel, for example such that some or all of the antimicrobial additive is surrounded or enclosed by the substance or material of the channel. The antimicrobial additive may be dispersed or distributed, for example dispersed or distributed homogeneously, throughout the substance or material of the channel or a part thereof, e.g. throughout a wall thickness of the tube or throughout a portion or fraction of a wall thickness of the tube (e.g. at least one quarter, in some examples at least one half, in one example at least three quarters of a wall thickness of the tube). It is noted that incorporation of an antimicrobial additive into the substance of the channel or liner (also referred to herein as "impregnation" of the channel or liner by the additive) is intended only as an adjunct antimicrobial scheme and is not intended to replace a primary disinfection strategy (e.g., HLD). Further embodiments disclosed herein include a channel for an endoscope (e.g., any of a suction control channel, a suction supply channel, an air channel, a water channel, an air supply channel, a water supply channel, or a water jet channel), or a liner for such a channel for an endoscope, that is made of a tube of PTFE and incorporates an antimicrobial additive. Further embodiments disclosed herein include endoscopes having one or more channels that are made of a tube of PTFE (or another thermoplastic polymer) and incorporate an antimicrobial additive. Further embodiments disclosed herein include methods of reprocessing (e.g., cleaning and/or disinfecting) and/or sterilizing such endoscopes that include one or more of the cleaning, disinfecting, and/or sterilizing methods described herein and/or any other known method of cleaning, disinfecting, and/or sterilizing an endoscope.

The antimicrobial additive includes silver ions as an active antimicrobial agent and comprises a substance ("carrier") that carries the silver ions and from which the silver ions may readily be released (e.g., in an ion-exchange reaction and/or by melting of the carrier). The carrier may for example be incorporated into the PTFE prior to sintering of the PTFE tube (e.g., by mixing a powder of the carrier into the PTFE powder prior to extrusion). Accordingly, a carrier that can withstand the high temperatures of the PTFE sintering process is desired. The melting temperature of PTFE is 342 degrees Celsius, and it may be desired to use a carrier that can withstand temperatures up to 400 degrees Celsius. The example carriers described below (zeolite and phosphate glass) can typically withstand temperatures up to 600 degrees Celsius.

One example of a suitable carrier is a zeolite, defined as any one or more of a class of aluminosilicate minerals which are bio-compatible and have a microporous structure that can accommodate the silver cations. The amount of silver ions in a zeolite carrier may be in a range of from about 0.5% to about 20% (e.g., in some examples from about 1% to about 10%, in one example from about 2% to about 5%, e.g. about 2.5%) by weight of the carrier. The size of the particles of a carrier powder may be expected to affect the rate of release of the silver ions from the carrier. The median size of the particles in a zeolite carrier may be in a range of about two to about four microns, in one example in a range of about 2.5 to about 3.5 microns.

Another example of a suitable carrier is a phosphate glass, defined as any one or more of a class of glasses that are bio-compatible and have a glass-forming substrate of phosphorus pentoxide (or a polymorph thereof) rather than silicon dioxide. Phosphate glasses are bio-soluble materials that may be doped with silver ions, which are incorporated into the glass structure rather than being a separate phase, and can be thus used to deliver silver ions in a controlled manner (e.g., according to a rate of degradation of the glass). The amount of silver ions in a phosphate glass carrier may be in a range of from about 0.5% to about 15% (in some examples from about 0.5% to about 5%, in one example from about 0.5% to about 2%, e.g., about 0.9%) by weight of the carrier. The median size of the particles in a phosphate glass carrier may be in a range of about ten to about forty microns, in one example in a range of about twenty to about thirty microns. A desired melting rate (e.g., rate of degradation) of a phosphate glass carrier may be achieved by selecting the composition of the glass by known methods.

The silver ions may be released from the carrier in an aqueous environment (e.g., upon contact with water or other fluids during use of the endoscope). In the case of a zeolite carrier, such release may occur via an ion-exchange reaction. In the case of a phosphate glass carrier, such release may occur via an ion-exchange reaction and/or by melting of the carrier.

As noted above, the antimicrobial additive may be incorporated into the PTFE as a powder prior to sintering (e.g., prior to extrusion). The amount (e.g. content or concentration) of carrier in the base material of the tube may be in a range of from 0.1 to 5% by weight of the base material (e.g., in a range of from 0.2 to 2%, or in a range of from 0.2 to 1%, or in a range of from 0.2 to 0.6%, or about 0.3%, or about 0.4%). The amount of the carrier in the tube (e.g. in the base material of the tube) may for example be at least 0.1%, in some examples at least 0.2%, in one example at least 0.5% by weight of the tube (or base material) and/or may for example be no more than 5%, in some examples no more than 2%, in one example no more than 1% by weight of the tube (or base material). The amount (e.g. content or concentration) of silver ions in the tube (e.g. in the base material of the tube) may be at least 0.0005% (five ten-thousandths of one percent), in some examples at least 0.001%, in one example at least 0.002%, in one example at least 0.003% by weight of the tube. The amount of silver ions in the carrier may be at least in some examples at least 1%, in one example at least 2%, in one example at least 5% by weight of the carrier and/or may be no more than 20%, in some examples no more than 15%, in one example no more than 10%, in one example no more than 5% by weight of the carrier. The base material may comprise virgin PTFE, or the base material may comprise PTFE modified with one or more fillers and/or other enhancements. The amount of carrier in the base material may be selected to provide a desired antimicrobial effect while retaining desired mechanical properties of the resulting PTFE tube such as desired degrees of flexibility, stiffness, and/or resistance to kinking and collapse.

By incorporating the silver ions within the wall of the tube (e.g., rather than within a coating on a surface of the tube), it may be expected that the resulting antimicrobial effect will have a higher durability than if the silver ions were incorporated into a coating applied to an interior surface of the tube. Microdamage to the interior surface of the channel (e.g., as may occur during use and/or cleaning as described herein) may even serve to replenish the supply of antimicrobial material present on the interior surface of the tube by exposing more of the incorporated silver ions within the tube wall to the interior environment of the channel.

A silver-ion-impregnated channel according to embodiments as described herein may be implemented to have an antimicrobial efficacy of the interior surface of the tube that persists during use of an endoscope having the channel (e.g., that may be retained after a large number (50, 100, 200, etc.) of cleaning cycles). Such antimicrobial efficacy may be indicated as a log reduction of *Escherichia coli* (in colony forming units (CFU)) of not less than 5.0, not less than not less than 6.0 or not less than 6.2 and/or as a log reduction of *Staphyrococcus aureus* (in CFU) of not less than 3.0, not less than 3.5, or not less than 3.7. Persistence of the antimicrobial efficacy may be indicated as a change not greater than 0.6, not greater than 0.8, not greater than 1.0, or not greater than 1.2 in such a log reduction over a predetermined number (e.g., 50, 100, 200) of cleaning cycles. Additionally or alternatively, a silver-ion-impregnated channel according to embodiments as described herein may be implemented to have a high degree of biocompatibility (e.g., a viability of at least 95, of at least 96, of at least 97, or of at least 98 percent as determined according to the method for testing for cytotoxicity as defined in International Standard ISO 10993-5 Annex C).

In tests of PTFE tubes having concentrations of a silver-ion-carrying carrier of 0.6% and 0.9% by weight of the tube, antimicrobial efficacy of the interior surface of the tube was retained after two hundred cleaning cycles. The antimicrobial efficacy was determined using the method of testing for antimicrobial activity of plastics as defined in International Standard ISO 22196 (International Organization for Standardization). Specifically, for PTFE tubes having concentrations of a silver-ion-carrying carrier of 0.6% and 0.9% by weight of the tube, log reduction of *Escherichia coli* (in colony forming units (CFU)) was found to be 7.1 initially and 6.3 after two hundred cleaning cycles, and log reduction of *Staphyrococcus aureus* (in CFU) was found to be 4.3 initially and 3.7 after two hundred cleaning cycles. Such tubes were also found to have a high degree of biocompatibility (e.g., viability>=98.9% as determined according to the method for testing for cytotoxicity as defined in International Standard ISO 10993-5 Annex C).

A silver-ion-impregnated channel according to embodiments as described herein may also be implemented as a liner or as an interior layer of a two-layer tube. A portion of the silver-ion-impregnated channel that is to be connected to another part of the endoscope (e.g., to a nozzle or other part of the insertion portion) may be etched to facilitate cohesive bonding (e.g., gluing) to such other part of the endoscope. The silver-ion-impregnated channel may be wire-wrapped or otherwise reinforced. The silver-ion-impregnated channel may be implemented as an original part of the endoscope or as a retrofit.

The principles described herein may be practiced as described to obtain implementations of silver-ion-impregnated channels for endoscopes, and endoscopes including one or more silver-ion-impregnated channels, that provide advantages such as inhibiting biofilm formation, providing a durable antimicrobial effect, and/or serving as an adjunct supporting feature to a cleaning and disinfection routine.

Further exemplary embodiments are provided below:

Example 1 includes a channel for an endoscope, the channel being a working channel and comprising a tube made of polytetrafluoroethylene (PTFE) having at least one additive, wherein: the at least one additive includes a carrier that contains silver ions and is incorporated within a wall of the tube, and a content of silver ions in the tube is at least 0.0005% by weight of the tube.

Example 2 includes a channel for an endoscope, the channel comprising a tube made of polytetrafluoroethylene (PTFE) having at least one additive, wherein: the channel is at least one among an air channel for an endoscope, a water channel for an endoscope, or a working channel for an endoscope; the at least one additive includes a carrier that contains silver ions and is incorporated within a wall of the tube; and a content of silver ions in the tube is at least 0.0005% by weight of the tube.

Example 3 includes the channel according to any one of Examples 1 and 2, wherein: a content of the carrier in the tube is at least 0.1% by weight of the tube; and a content of silver ions in the carrier is at least 0.5% by weight of the carrier.

Example 4 includes the channel according to any of Examples 1-3, wherein a content of the carrier in the tube is not more than 1% by weight of the tube.

Example 5 includes the channel according to any of Examples 1-4, wherein the carrier is dispersed throughout a wall thickness of the tube.

Example 6 includes the channel according to any of Examples 1-5, wherein the carrier is embedded within the wall of the tube.

Example 7 includes the channel according to any of Examples 1-6, wherein the carrier comprises a phosphate glass.

Example 8 includes the channel according to Example 7, wherein a content of silver ions in the carrier is not more than 15% by weight of the carrier.

Example 9 includes the channel according to any of Examples 1-8, wherein the carrier comprises a zeolite.

Example 10 includes the channel according to Example 9, wherein a content of silver ions in the carrier is not more than 20% by weight of the carrier.

Example 11 includes the channel according to any of Examples 1-10, wherein:
the tube is made by sintering PTFE, and
the carrier is incorporated into the PTFE before the sintering.

Example 12 includes the channel according to any of Examples 1-11, wherein an inner diameter of the tube is at least four millimeters.

Example 13 includes the channel according to any of Examples 1-12, wherein an inner diameter of the tube is not more than two millimeters.

Example 14 includes an endoscope comprising the channel according to any of Examples 1-13 as a working channel.

Example 15 includes a method of cleaning the endoscope of Example 14, the method comprising passing a brush within an interior lumen of the working channel.

Example 16 includes the method of Example 15, the method further comprising soaking the endoscope in a disinfecting solution that contains at least one high-level disinfectant.

Example 17 includes the method of any of Examples 15 and 16, the method further comprising exposing the interior lumen of the working channel to vaporized hydrogen peroxide.

Example 18 includes an endoscope comprising at least one channel according to any of Examples 1-13.

Example 19 includes a method of reprocessing the endoscope of Example 18, the method comprising exposing an interior lumen of the at least one channel to at least one of: a disinfecting solution that contains at least one high-level disinfectant, or a cleaning solution that contains at least one detergent or enzymatic cleaning agent.

Example 20 includes a method of reprocessing the endoscope of Example 19, the method further comprising exposing an interior lumen of the at least one channel to vaporized hydrogen peroxide.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. For the purposes of the present document, the phrase "A is based on B" means "A is based on at least B." As used herein, the term "substantially," "approximately," or "about" may be substituted with "within [a percentage] of" what is specified, where the percentage includes 0.1, 1, 5, and 10 percent. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An endoscope comprising:
at least one channel comprising a tube made of polytetrafluoroethylene (PTFE) having at least one additive, wherein:
the at least one additive includes a carrier that contains silver ions and is incorporated within a wall of the tube;
the tube does not comprise a zeolite;
a content of silver ions in the tube is at least 0.0005% by weight of the tube; and
the at least one channel is a working channel of the endoscope the working channel from repeated usage and cleanings.

2. The endoscope according to claim 1, wherein:
a content of the carrier in the tube is at least 0.1% by weight of the tube; and
a content of silver ions in the carrier is at least 0.5% by weight of the carrier.

3. The endoscope according to claim 1, wherein a content of the carrier in the tube is not more than 1% by weight of the tube.

4. The endoscope according to claim 1, wherein the carrier is dispersed throughout a wall thickness of the tube.

5. The endoscope according to claim 1, wherein the carrier is embedded within the wall of the tube.

6. The endoscope according to claim 1, wherein the carrier comprises a phosphate glass.

7. The endoscope according to claim 6, wherein a content of silver ions in the carrier is not more than 15% by weight of the carrier.

8. The endoscope according to claim 1, wherein:
the tube is made by sintering PTFE, and
the carrier is incorporated into the PTFE before the sintering.

* * * * *